US00PP18079P2

(12) United States Plant Patent
Meulenbroek

(10) Patent No.: US PP18,079 P2
(45) Date of Patent: Sep. 25, 2007

(54) STRAWBERRY PLANT NAMED 'FIGARO'

(50) Latin Name: *Fragaria L.*
Varietal Denomination: Figaro

(75) Inventor: Egbertus Joseph Meulenbroek, Zetten (NL)

(73) Assignee: Plant Research International, B.V., Wageningen (NL)

( * ) Notice: Subject to any disclaimer, the term of this patent is extended or adjusted under 35 U.S.C. 154(b) by 37 days.

(21) Appl. No.: 11/188,966

(22) Filed: Jul. 25, 2005

(51) Int. Cl.
*A01H 5/00* (2006.01)

(52) U.S. Cl. ..... Plt./208
(58) Field of Classification Search ..... Plt./208
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of Strawberry plant named 'Figaro', characterized by its vigorous growth habit; large and uniformly rounded fruits; very firm fruits; glossy light red-colored fruits; and pleasant fruit aroma and taste.

1 Drawing Sheet

Botanical designation: *Fragaria L.*
Cultivar denomination: 'Figaro'.

BACKGROUND OF THE INVENTION

The present Invention relates to a new and distinct cultivar of Strawberry plant, botanically known as *Fragaria L.*, and hereinafter referred to by the name 'Figaro'.

The new Strawberry is a product of a planned breeding program conducted by the Inventor in Wageningen, The Netherlands. The objective of the breeding program was to develop new high-yielding Strawberry cultivars with good fruit quality, good postharvest longevity and ease of harvesting.

The new Strawberry originated from a cross-pollination made by the Inventor during the summer of 1991 of the *Fragaria L.* cultivar Elsanta, not patented, as the female, or seed, parent with the *Fragaria L.* cultivar Pajaro, not patented, as the male, or pollen, parent. The new Strawberry was discovered and selected by the Inventor from within the resultant progeny from the above-mentioned cross-pollination in a controlled environment in Wageningen, The Netherlands during the summer of 1993.

Asexual reproduction since the fall of 1993 of the new cultivar by cuttings in a controlled environment in Elst, The Netherlands, has shown that the unique features of this new Strawberry are stable and reproduced true to type in successive generations.

SUMMARY OF THE INVENTION

The following traits have been repeatedly observed and are determined to be the unique characteristics of 'Figaro'. These characteristics in combination distinguish 'Figaro' as a new and distinct cultivar:

1. Vigorous growth habit.
2. Large and uniformly rounded fruits.
3. Very firm fruits.
4. Glossy light red-colored fruits.
5. Pleasant fruit aroma and taste.

Plants of the new Strawberry can be compared to plants of the female parent, the cultivar Elsanta. Plants of the new Strawberry differ from plants of the cultivar Elsanta in the following characteristics:

1. Plants of the new Strawberry have smaller and lighter green-colored leaves than plants of the cultivar Elsanta.
2. Plants of the new Strawberry had smaller flowers than plants of the cultivar Elsanta.
3. Fruits of plants of the new Strawberry are more rounded and firmer than fruits of plants of the cultivar Elsanta.
4. Fruits of plants of the new Strawberry are light red in color whereas fruits of plants of the cultivar Elsanta are brownish red in color.

Plants of the new Strawberry can be compared to plants of the male parent, the cultivar Pajaro. Plants of the new Strawberry differ from plants of the cultivar Pajaro in the following characteristics:

1. Plants of the new Strawberry are more vigorous and larger than plants of the cultivar Pajaro.
2. Fruits of the plants of new Strawberry are more rounded and firmer than fruits of plants of the cultivar Pajaro.
3. Fruits of plants of the new Strawberry are light red in color whereas fruits of plants of the cultivar Pajaro are red in color.

Plants of the cultivar Figaro can be compared to the cultivar Valeta, not patented. However, in side-by-side comparisons conducted in Wageningen, The Netherlands, plants of the new Strawberry and the cultivar Valeta differed in the following characteristics:

1. Plants of the new Strawberry had lighter green-colored leaves than plants of the cultivar Valeta.
2. Fruits of plants of the new Strawberry were larger, more rounded and firmer than fruits of plants of the cultivar Valeta.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description, which accurately describe the actual colors of the new Strawberry. The photograph comprises a side view of the base of typical plant and fruit of 'Figaro' grown in an outdoor nursery.

DETAILED BOTANICAL DESCRIPTION

Plants of the cultivar Figaro have not been observed under all possible environmental conditions. The phenotype may vary somewhat with variations in environment such as temperature, light intensity and daylength without, however, any variance in genotype.

In the following description, color references are made to The Royal Horticultural Society Colour Chart, 2001 Edition, except where general terms of ordinary dictionary significance are used. Plants used for the aforementioned photograph and following description were grown in an outdoor nursery under conditions that closely approximate commercial production conditions during the spring and summer in Wageningen, The Netherlands. During the production of the plants, day temperatures ranged from 12° C. to 30° C. and night temperatures ranged from 0° C. to 20° C. Plants were about one year old when the photograph and description were taken.

Botanical classification: *Fragaria L.* cultivar Figaro.

Parentage:

*Female parent.*—*Fragaria L.* cultivar Elsanta, not patented.

*Male parent.*—*Fragaria L.* cultivar Pajaro, not patented.

Propagation:

*Type.*—By cuttings.

*Root description.*—Fine, fibrous and well-branched; light brown in color.

Plant description:

*Plant form/habit.*—Upright and open plant habit. Plants globose in form. Leaves basal, dense and bushy plant habit. Vigorous growth habit; rapid growth rate. Few crowns per plant.

*Plant height.*—About 25 to 30 cm.

*Plant diameter.*—About 35 to 40 cm.

*Foliage description.*—Arrangement: Basal rosette; compound with typically three leaflets. Length: About 8 to 12 cm. Width: About 6 to 10 cm. Shape: Broadly ovate. Apex: Obtuse. Base: Obtuse to rounded. Margin: Serrate. Texture, upper and lower surfaces: Pubescent. Venation: Pinnate. Color: Developing foliage, upper surface: 138A. Developing foliage, lower surface: 144A. Fully developed foliage, upper surface: 137A; venation, 137A. Fully developed foliage, lower surface: 137C; venation, 144C. Petiole length: About 8 to 12 cm. Petiole diameter: About 2 to 3 mm. Petiole color, upper and lower surfaces: 146B.

Flower description:

*Flower type and habit.*—Rotate flowers arranged singly at lateral apices. Flowers held beneath the leaf canopy. Flowers not fragrant.

*Natural flowering season.*—Early flowering; plants begin flower late April to early May in The Netherlands.

*Flower size.*—Diameter: Large, about 3 to 3.5 cm. Depth (height): About 5 mm.

*Petals.*—Arrangement: Single whorl of five petals, not imbricate. Length: About 1.5 cm. Width: About 1.5 cm. Shape: Roughly spatulate. Apex: Rounded. Base: Attenuate. Margin: Entire. Texture, upper and lower surfaces: Smooth, glabrous; satiny. Color: When opening and fully opened, upper surface: 155D. When opening and fully opened, lower surface: 155D.

*Sepals.*—Arrangement: Single whorl of 10 to 12 sepals, star-shaped calyx; calyx situation level with the surface; attitude of the calyx segments is spreading and slightly smaller than fruit diameter. Adherence of the calyx is medium to strong. Length: About 1.5 cm. Width: About 5 mm. Shape: Lanceolate. Apex: Acute. Base: Fused. Margin: Entire. Texture, upper and lower surfaces: Pubescent. Color, upper and lower surfaces: Close to 137A.

*Peduncles.*—Length: About 6 to 8 cm. Diameter: About 1 to 2 mm. Strength: Strong. Color: 144B.

*Reproductive organs.*—Stamens: Quantity per flower: About 30. Anther length: About 2 mm. Anther color: 14B to 14C. Pollen amount: Abundant. Pollen color: 15C. Pistils: Quantity per flower: About 30. Stigma shape: Rounded. Stigma color: Close to 5A. Fruits: Time of fruiting: During June in The Netherlands. Keeping quality: About five to ten days. Length: Large, about 5 to 6 cm. Diameter: About 3.5 to 4.5 cm. Shape: Rounded cordate; uniform. Truss length: Relatively long; flowers level to the foliage. Hollow center size: Weekly expressed. Firmness: Very firm. Fragrance, taste: Sweet, pleasant. Luster: Glossy. Color: 34A to 34B. Flesh color: 34A. Achene insertion: Level with the fruit surface. Achene color: 1A; on shoulders of the fruit when exposed to light, 33A.

Disease/pest resistance: Plants of the new Strawberry have not been noted to be resistant to pathogens and pests common to Strawberry.

Temperature tolerance: Plants of the new Strawberry have been observed to tolerate temperatures ranging from 0° C. to 35° C.

It is claimed:

1. A new and distinct cultivar of Strawberry plant named 'Figaro', as illustrated and described.

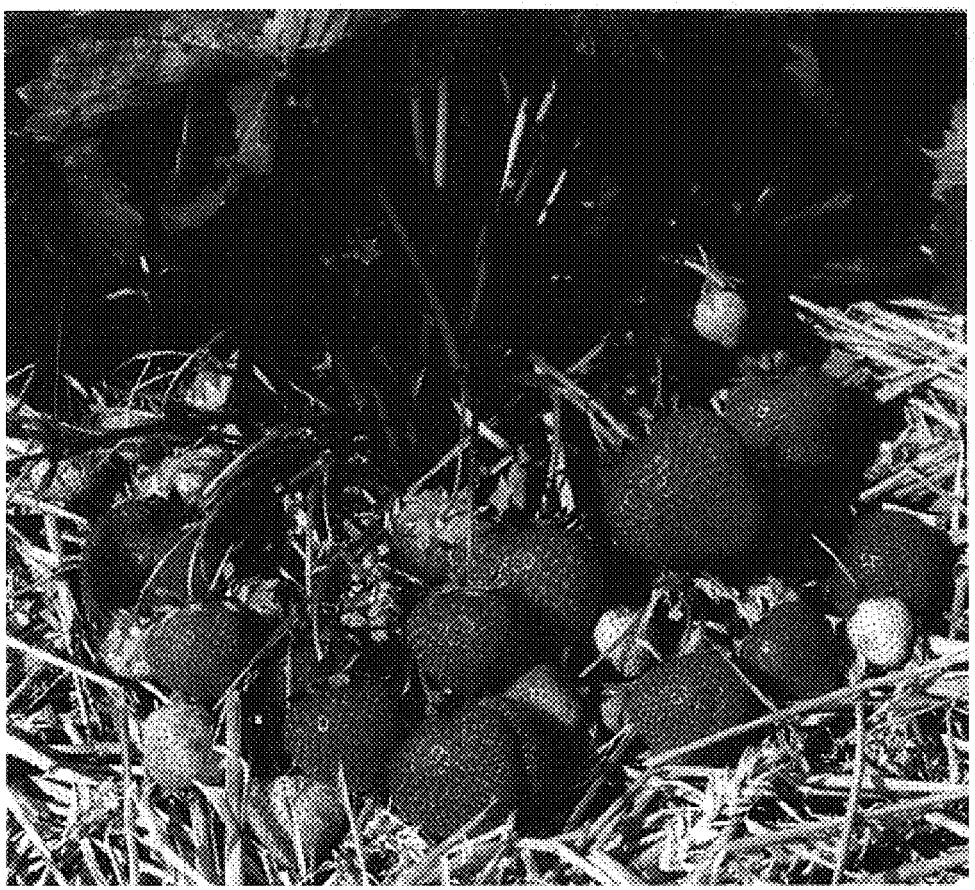

* * * * *